United States Patent [19]
Lahanas et al.

[11] Patent Number: 6,114,424
[45] Date of Patent: Sep. 5, 2000

[54] OPALESCENT COSMETIC COMPOSITIONS AND METHODS FOR THEIR PREPARATION

[75] Inventors: Konstantinos M. Lahanas, Paramus, N.J.; Daniela Toma, Floral Park; Gheorghe Cioca, Lake Grove, both of N.Y.

[73] Assignee: Estee Lauder, Inc., New York, N.Y.

[21] Appl. No.: 09/015,384

[22] Filed: Jan. 29, 1998

[51] Int. Cl.[7] .................. C08K 5/09; C08K 5/10; A61K 7/44; A61K 31/74

[52] U.S. Cl. .................. 524/286; 524/300; 524/315; 524/321; 524/384; 424/60; 424/78.03; 424/78.31; 424/401

[58] Field of Search ................... 524/286, 300, 524/315, 321, 384; 424/60, 78.03, 78.31, 401

[56] References Cited

U.S. PATENT DOCUMENTS

| | | | |
|---|---|---|---|
| 3,907,581 | 9/1975 | Wilcox | 106/193 J |
| 3,948,845 | 4/1976 | Marx et al. | 264/4 |
| 4,594,359 | 6/1986 | Padfield et al. | 514/647 |
| 4,722,835 | 2/1988 | Schamper et al. | 424/66 |
| 4,725,430 | 2/1988 | Schamper et al. | 424/66 |
| 4,753,829 | 6/1988 | Panush | 427/385.5 |
| 4,861,676 | 8/1989 | Lee | 428/516 |
| 4,947,792 | 8/1990 | Kaminski | 119/5 |
| 5,250,291 | 10/1993 | Park et al. | 424/66 |
| 5,368,848 | 11/1994 | Brazinsky | 424/65 |

FOREIGN PATENT DOCUMENTS 3-296584  12/1991  Japan .

*Primary Examiner*—Kriellion Sanders
*Attorney, Agent, or Firm*—Fish & Neave; Richard M. Barnes; Brett G. Alten

[57] ABSTRACT

The present invention relates to opalescent cosmetic compositions that are stable and suitable for topical application to human skin, and to methods for preparing and using such compositions. The compositions of the invention include (1) a hydrogenated indene-styrene-vinyltoluene polymer in an amount from about 0.1% by weight to about 50% by weight of the composition and (2) a carrier material in an amount from about 50% by weight to about 99.9% by weight of the composition. The opalescent composition may further contain a cosmetic material in an amount from about 0.5% by weight to about 20% by weight of the composition.

33 Claims, No Drawings

OPALESCENT COSMETIC COMPOSITIONS AND METHODS FOR THEIR PREPARATION

TECHNICAL FIELD OF THE INVENTION

This invention relates to opalescent cosmetic compositions. More particularly, this invention relates to compositions that, when applied topically to human skin, exhibit an aesthetically pleasing opalescent quality, and to methods for making and using such compositions.

BACKGROUND OF THE INVENTION

Cosmetics typically are intended to provide an attractive appearance through the use of color, e.g., by highlighting certain features of the face and/or accentuating natural colors. Colored cosmetics are used, for example, to accentuate lines of separation (eye liners and lip liner), to provide sensuous color to portions of the skin (lipsticks and glosses), and to provide a "healthy glow" to the cheeks (blushes and rouges). Cosmetics may also protect the skin (e.g., by blocking the skin from harmful ultraviolet light). A variety of coloring agents can also be used to color cosmetics, including inorganic and organic dyes or pigments.

Compositions having an opalescent quality are desirable because of their aesthetic light-reflecting properties. One known opalescent composition is described in Marx et al. U.S. Pat. No. 3,948,845, which uses copolymers of one or more monovinyl-substituted aromatic compounds with one or more copolymerizable conjugated dienes. That composition is encapsulated in transparent containers and sealed for use in various decorative effects, such as jewelry, and reflective signal devices. Another opalescent composition is described in Willcox U.S. Pat. No. 3,907,581. That composition is solid and comprised of a substantially clear, colorless organic polymeric solid matrix and particles of titanium dioxide dispersed therein. The solid composition described by Willcox was designed for making decorative opalescent objects and forms, such as solid films, hard lacquers, and nylon fibers.

Although Marx et al. and Willcox describe opalescent compositions, they do not describe compositions comprising hydrogenated indene-styrene-vinyltoluene polymers. In fact, as far as applicants are aware, such polymers have never been used to provide an opalescent quality to any composition, let alone one suitable for topical application to human skin. Rather, these hydrogenated polymers have been used as tackifiers, such as for use with pressure sensitive adhesive tapes and hot melt systems. See, for example, U.S. Pat. No. 4,861,676 and Japanese Patent No. 3 296 584.

It is therefore an object of the present invention to provide aesthetically pleasing compositions that have an opalescent quality and are suitable for topical application to human skin.

It is also an object of the present invention to provide opalescent cosmetic compositions that contain hydrogenated indene-styrene-vinyltoluene polymers.

An additional object of this invention is to provide methods for preparing and using such compositions.

SUMMARY OF THE INVENTION

The opalescent cosmetic compositions of the present invention comprise:
(1) at least one hydrogenated indene-styrene-vinyltoluene polymer in an amount from about 0.1% by weight to about 50% by weight of the composition;
(2) a carrier material in an amount from about 50% by weight to about 99.9% by weight of the composition; and preferably, but not necessarily,
(3) an additional cosmetic material in an amount from about 0.5% by weight to about 20% by weight of the composition.

A hydrogenated indene-styrene-vinyltoluene polymer, as used herein, is any hydrogenated indene-styrene-vinyltoluene polymer that has a softening point of between about 70° C. and about 140° C.

A carrier material, as used herein, includes any material in which a hydrogenated indene-styrene-vinyltoluene polymer is miscible and suitable for topical application to human skin. Carrier materials may include solvents, such as octyl methoxycinnamate, phenoxy ethanol, benzyl alcohol, phenyl trimethicone, methyl benzoate, and mixtures thereof. A preferred carrier material of the invention is octyl methoxycinnamate. Carrier materials of this invention may also include one or more solutes, such as truxillic acid, ferulic acid, and ethyl ferulate, which are soluble in the above-identified solvents at elevated temperatures. Carrier materials may also include (a) one or more lipophilic oils, such as castor oil, mineral oil, squalene, fatty acids (e.g., oleic acid), fatty alcohols (e.g., octyldodecanol), a $C_{12-15}$ alkyl benzoate, a propylene glycol dipelargonate, a glycerol trioctanoate and mixtures thereof, and/or (b) one or more lipophilic waxes, such as insect waxes, such as beeswax, animal waxes, such as lanolin, plant waxes, such as carnauba, mineral waxes, such as ozokerite, petroleum waxes, such as paraffin wax, synthetic waxes, such as polyethylene, and mixtures thereof.

Additional cosmetic materials that may be used in the composition of the invention include any material that is miscible in a carrier material and is used as a cosmetic material, e.g., a colorant, fragrance, sunscreen, and/or dermatologic agent.

The compositions of the invention may be made by a method which comprises the steps of:
(a) mixing the polymer with the carrier fluid at a temperature and for a period of time sufficient (e.g., at a temperature of between about 75° C. and about 200° C. for about 15 min to about 45 min) to dissolve the DBMSA in the carrier fluid to form a solution;
(b) mixing a cosmetic material selected from the group consisting of colorants, fragrances, sunscreens, dermatologic agents and mixtures thereof with the solution to form the composition, the amounts of DBMSA, carrier fluid, and cosmetic material being adjusted such that the resulting mixture contains:
  (i) the polymer in an amount from about 0.1% by weight to about 50% by weight of the composition,
  (ii) the carrier material in an amount from about 50% by weight to about 99.9% by weight of the composition, and
  (iii) the cosmetic material in an amount from about 0.01% by weight to about 20.0% by weight of the composition; and
(c) cooling said composition to ambient temperature. Of course, when an additional cosmetic composition is not used, step (b) would not include mixing a cosmetic material with the solution.

It is to be understood that the step of mixing a cosmetic material, set forth above, may be conducted prior to mixing a polymer in the carrier material, or during or after the step of mixing of the polymer with the carrier material. It is also to be understood that step (a) may itself be conducted in steps. For example, the polymer may be first mixed with a solvent at a temperature and for a period of time sufficient to dissolve the polymer in the first component to form a first solution. Then, the first solution may be combined with a solute, or any other component, at a temperature and for a period of time sufficient to form a second solution. It should be understood that because the carrier material may have more than two components, additional steps may be required.

It will also be understood that the cosmetic material may be mixed with the other ingredients of the invention (e.g., the polymer of the carrier material) before or after the polymer is dissolved in the carrier material.

The compositions of the invention may use a lipophilic oil as the only or primary carrier material in the composition. Such compositions are substantially non-greasy and non-sticky.

DETAILED DESCRIPTION OF THE INVENTION

According to the present invention, opalescent compositions suitable for topical application to human skin and methods for making such compositions are provided.

An opalescent composition suitable for topical application to human skin contains: (1) a hydrogenated indene-styrene-vinyltoluene polymer in an amount from about 0.1% by weight to about 50% by weight

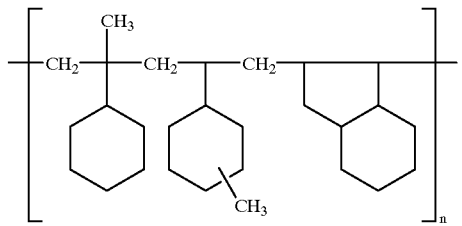

of the composition, (2) a carrier material in an amount from about 50% by weight to about 99.9% by weight of the composition, and preferably but not necessarily, (3) a cosmetic material in an amount from about 0.5% by weight to about 20% by weight of the composition.

As used herein, the term "hydrogenated indene-styrene-vinyltoluene polymer" means any hydrogenated polymer that includes an indene, a styrene, and a vinyltoluene. Preferably, the hydrogenated indene-styrene-vinyltoluene polymer has a softening point between about 70° C. and about 140° C., and most preferably between about 125° C. and about 140° C. Polymers of this type are sold under the trademark Arkon™, by Arakawa Chemical Industries, Ltd., of Osaka, Japan. One example of such a polymer that has a softening point of 125° C. is indene-α-methylstyrene-vinyltoluene polymer (Reg. No. 37191-34-7, also known as Arkon™ P-125). The generic structure for this polymer is represented by the following formula.

As used herein, a hydrogenated indene-styrene-vinyltoluene polymer (hereinafter, "polymer") can be a mixture of two or more such polymers having different softening points. Of course, the polymer may be formed during copolymerization.

As used herein, the term "carrier material" is any material, or combination of materials, that is miscible with the polymer and suitable for topical application to human skin. The carrier material may, for example, include one or more solvents, such as organic solvents. Organic solvents which may be used in accordance with this invention include, for example, octyl methoxycinnamate, phenyl trimethicone, phenoxy ethanol, benzyl alcohol, dibenzyl maleate, and methyl benzoate. These solvents are especially useful when making solid sticks with a gelling agent, such as DBMSA, because they are miscible at elevated temperatures with DBMSA.

Another class of carrier materials are lipophilic materials. A lipophilic material, as used herein, refers to a material that is miscible in lipids. One class of lipophilic materials that may be used in the present invention is the class known as cosmetically acceptable esters, e.g., mono-, di- and tri-esters having an alcohol chain length of 1 to 22 and an acid chain length of 1 to 22. Persons skilled in the art recognize that the group of cosmetically acceptable esters is very large, and can be further subdivided into, e.g., oils, waxes, glyceryl esters aliphatic esters and fats. See, e.g., *CFTA International Cosmetic Ingredient Dictionary*, 4th ed. (J. M. Nikitakis, et al. eds. Cosmetic, Toiletry and Fragrance Association, Inc. Washington, 1991).

Preferably, the carrier material is lipophilic and has a low to moderate polarity, such as esters and ethers. Therefore, although highly non-polar materials, such as hydrocarbons, may be used in accordance with this invention, they are preferably used at relatively low concentrations. Thus, a carrier material according to this invention might include an ester and/or an ether in relatively high concentration(s) and a hydrocarbon in a relatively low concentration.

Furthermore, it is preferable that the index of refraction of the carrier material is high (e.g., greater than or equal to about 1.5). The index of refraction of the carrier material may be measured by using a refractometer and by employing conventional refractometry techniques. A particularly preferred refractometer for the determination of the index of refraction of materials used in accordance with this invention is Fisher Scientific's Abbe Refractometer Model No. 6182 (This and other models of Abbe refractometers are commercially available from Fisher Scientific, of Springfield, N.J.).

As used herein, the term "lipophilic oils" refers to lipophilic materials that are liquid at room temperature to about 25° C. Preferred lipophilic oils for use in the invention are selected from the group consisting of castor oil, mineral oil, squalene, fatty acids (e.g., oleic acid), fatty alcohols (e.g., octyldodecanol), a $C_{12-15}$ alkyl benzoate, a propylene glycol dipelargonate, a glycerol trioctanoate and mixtures thereof.

As used herein, the term "lipophilic waxes" refers to lipophilic materials that are solid at room temperature, but melt at elevated temperatures. Where non-greasy and non-sticky compositions are preferred, no more than about 20% by weight of the carrier material is one or more lipophilic waxes. Preferred lipophilic waxes are those selected from the group consisting of insect waxes, such as beeswax, animal waxes, such as lanolin, plant waxes, such as carnauba, mineral waxes, such as ozokerite, petroleum waxes, such as paraffin wax, synthetic waxes, such as polyethylene, and mixtures thereof.

As used herein, the term "cosmetic material" means any material selected from the group consisting of colorants, fragrances, sunscreens, dermatologic agents, and mixtures thereof. The use of one or more cosmetic materials allows compositions of the present invention to be formulated for a wide range of cosmetic applications. For example, the compositions may be formulated as lip area treatment preparations, eye area treatment preparations, sunscreen preparations, antiinflammatory preparations, antiacne preparations, antibacterial preparations, color cosmetic preparations, fragrance preparations, moisturizing preparations, exfoliating preparations, and the like.

Colorants useful in the composition of the invention include lipophilic dyes, lakes, pigments and mixtures thereof. Preferred fragrances are the essential oils. Dermatological agents that may be used in our compositions include vitamins, antiinflammatory agents, hydroxy acids, and the like, and mixtures thereof. Sunscreens that may be used include dioxybenzone, 2-ethylhexyl 2-cyano-3,3-diphenylacrylate, 2-ethylhexyl p-methoxycinnamate, 2-ethylhexyl salicylate, homosalate, menthyl anthranilate, oxybenzone, octyl dimethyl PABA, red petrolatum, titanium dioxide, ferulic acid esters, or mixtures thereof. Preferably the sunscreen is titanium dioxide, ferulic acid esters or mixtures thereof. Most preferably the sunscreen is titanium dioxide or ethyl ferulate or mixtures thereof. A preferable sunscreen for use in solid compositions is DBMSA because DBMSA is also a gelling agent.

The aesthetic and functional properties may be controlled by varying the compositions and amounts of compositions and amounts of the polymer, carrier material, and cosmetic material. An aesthetic property that may be controlled by a person skilled in the art by varying the composition and amount of polymer includes the degree of opalescence. The aesthetic and functional properties may also be controlled by a person skilled in the art by varying the composition and amount of carrier material. These properties include at least the emollience, skin feel, and rate of absorbance through the skin.

Finally, the aesthetic and functional properties that may be controlled by a person skilled in the art by varying the composition and amount of the cosmetic material, which includes, for example, the color, fragrance, and/or Sun Protection Factor (SPF). The SPF of a composition can be measured using the in vivo method (See: "Sunscreen Products for Over-The-Counter Human Drugs, Proposed Safety, Effective and Labeling Conditions", Department of Health, Education, and Welfare, Food and Drug Admin., *Federal Register* 43(166), Part II, pp. 38206–38269 (1978)).

The carrier material used in compositions of this invention may also include other ingredients that are commonly employed by one of skill in the art in compositions for application to the skin (e.g., stabilizers, antimicrobial agents, antioxidants, and the like).

As mentioned above, DBMSA, a known gelling agent, may be added to the composition for increasing the viscosity of the composition, or even making the composition solid. In addition to serving as a gelling agent, DBMSA also has sun screening properties. The amount of DBMSA should be from about 2.0% by weight to about 20.0% by weight of the composition. DBMSA suitable for use in the invention may be obtained from a number of commercial sources. Among the commercially available sources of DBMSA are MIL-LITHIX™ 925 (obtained from Milliken Chemical, a division of Milliken & Company, Spartansburg, SC), GELL-All-D™ (obtained from New Japan Chemical Company, Ltd.), and DISORBENE™ (obtained from ROQUETTE Freres, France.)

Carrier materials suitable for use in the invention may be prepared from one or more components, including fluids and solids at room temperature, but liquid at elevated temperatures. Examples of liquids (e.g., solvents) that may be used as components of the carrier fluid include the class of liquids miscible at elevated temperatures with the polymer and DBMSA, such as octyl methoxycinnamate, phenyl trimethicone, phenoxy ethanol, benzyl alcohol, dibenzyl maleate, and methyl benzoate. Examples of solids (e.g., solutes) at room temperature that may be components of the carrier material are truxillic acid, ferulic acid, and ethyl ferulate. These solids are especially useful for the preparation of clear cosmetic sticks, as described in copending, commonly-assigned U.S. patent application Ser. No. 08/666,750, filed Jun. 19, 1996, which is hereby incorporated by reference in its entirety.

In a preferred embodiment of making the compositions of this invention, the polymer and the carrier material are combined and heated at a temperature sufficient to dissolve substantially all the polymer before one or more cosmetic materials are added to the mixture. Preferably, the temperature used is about 75° C. to about 200° C., and most preferably about 100° C. to about 150° C. Once substantially all the polymer is in solution, the cosmetic material may be combined with the solution and the resulting mixture is cooled to room temperature. Particularly when the cosmetic material is colored or particulate, proceeding in this manner facilitates the ability of the person(s) making the composition to determine that substantially all the polymer is dissolved in the solution.

When the composition is solid at room temperature, the cooling step is preferably conducted after the composition is transferred, while still above ambient temperature, to the container in which it will be stored. For example, heated, still liquid material may be transferred to a lipstick mold, a makeup pan, or a wide-mouthed jar and cooled to ambient temperature to solidify the mixture.

Another method for preparing compositions of the present invention includes at least two steps. The first step involves mixing the polymer and the carrier material. The solvent which, when combined with the polymer at a temperature and for a period of time (e.g., about 15 min to about 45 min), is sufficient to dissolve the polymer in the solvent to form a first solution without burning. Solvents which may be used in accordance with this invention, include, but are not limited to, the organic solvents already described above. Then, the first solution may be mixed with a cosmetic material at a temperature and for a period of time (e.g., about 15 min to about 45 min) sufficient to dissolve the first solution in the cosmetic material to form the opalescent composition. Of course, the polymer, carrier material, and cosmetic material may be mixed at once at a lower temperature, such as at room temperature, if all three components are miscible at that temperature. Thereafter, the resulting composition is cooled to ambient temperature.

The following non-limiting examples illustrate various compositions of the present invention.

EXAMPLES

Example 1

A Clear Opalescent Carrier Fluid

| Component | | Parts By Weight |
|---|---|---|
| Polymer | Arkon ™ P-125[1] | 20.0 |
| Carrier Material | Octyl methoxycinnamate | 80.0 |

[1]Arkon ™ P-125 is an Indene-α-methylstyrene-vinyltoluene polymer.

Procedure:

The Arkon™ polymer and carrier material were blended at 150° C. using a LIGHTNIN™ Mixer until a clear opalescent fluid was obtained. The fluid was then cooled to room temperature.

The composition of Example 1 is useful for providing an aesthetically pleasing carrier fluid, such as fluids for carrying fragrances, sunscreens, and the like.

Example 2

A Clear Lipstick with Opalescence and Color

| Component | | Parts By Weight |
|---|---|---|
| Polymer: | Arkon ™ P-125 | 10.0 |
| Carrier Material: | Phenoxy ethanol | 75.0 |
| | DBMSA | 14.5 |
| Cosmetic Material | D & C Red No. 21 6921/362[2] | 0.5 |

[2] A D&C Red No. 21-containing composition obtained from Sun Chemical Corp.

Procedure:

The phenoxy ethanol and DBMSA were blended at 175° C. using a LIGHTNIN™ Mixer until a clear solution was obtained. The Arkon™ polymer and D & C Red No. 21 6921/362 were then mixed into this solution. The resultant mixture was poured into a mold and cooled to room temperature.

Example 3

A Clear Lipstick with Opalescence

| Component | | Parts By Weight |
|---|---|---|
| Polymer | Arkon ™ P-125 | 15.0% |
| Carrier Material | Octyl methoxycinnamate | 80.0 |
| Cosmetic Material | DBMSA | 5.0 |

Procedure:

The octyl methoxycinnamate and DBMSA were heated to 175° C. and mixed with the Arkon™ polymer using a LIGHTNIN™ Mixer. The resultant mixture was poured into a lipstick mold and cooled to room temperature.

The composition of Example 3 is useful for providing an aesthetically pleasing, non-sticky, non-greasy, clear, and opalescent composition to the lip area.

Example 4

An Opalescent Sunscreen Stick

| Component | | Parts By Weight |
|---|---|---|
| Polymer: | Arkon ™ P-125 | 20.0 |
| Carrier Material: | Phenyl trimethicone | 67.5 |
| | Octyl methoxycinnamate | 7.5 |
| Cosmetic Material | DBMSA | 5.0 |

Example 5

An Opalescent Sunscreen Stick

| Component | | Parts By Weight |
|---|---|---|
| Polymer: | Arkon ™ P-125 | 20.0 |
| Carrier | Phenyl trimethicone | 65.5 |
| Material: | Salicylic acid USP (Powder)[3] | 2.0 |
| | Octyl methoxycinnamate | 7.5 |
| Cosmetic Material | DBMSA | 5.0 |

[3] A salicylic acid-containing composition obtained from Rhone-Poulenc Inc.

Example 6

An Opalescent Sunscreen Stick

| Component | | Parts By Weight |
|---|---|---|
| Polymer: | Arkon ™ P-125 | 15.0 |
| Carrier | Octyl methoxycinnamate | 65.0 |
| Material: | 3-methyl 2-oxazolidone | 15.0 |
| Cosmetic Material | DBMSA | 5.0 |

Example 7

An Opalescent Sunscreen Stick

| Component | | Parts By Weight |
|---|---|---|
| Polymer: | Arkon ™ P-125 | 15.0 |
| Carrier | Finsolve TN[4] | 60.0 |
| Material: | Ferulic acid | 20.0 |
| Cosmetic Material | DBMSA | 5.0 |

[4] A $C_{12-15}$ alkyl benzoate-containing composition obtained from Finetex, Inc.

Example 8

A Solid Opalescent Fragrance Stick

| Component | | Parts by Weight |
|---|---|---|
| Polymer: | Arkon ™ P-125 | 15.0 |
| Carrier | Emerest 2388[5] | 80.0 |
| Material: | DBMSA | 4.5 |
| Cosmetic Material | Fragrance | 0.5 |

[5] A propylene glycol dipelargonate-containing composition obtained from Henkel Corp.

The Emerest 2388 and DBMSA were blended at 175° C. using a LIGHTNIN™ Mixer until a clear solution was obtained. The fragrance and Arkon™ polymer was then mixed into this solution. The resultant mixture was poured into a mold and cooled to room temperature.

While the present invention has been set forth in terms of specific embodiments thereof, it will be understood that the invention is the defined by the appended claims.

We claim:

1. An opalescent composition suitable for topical application to human skin comprising:

(1) at least one hydrogenated indene-styrene-vinyltoluene polymer in an amount from about 0.1% by weight to about 50% by weight of the composition; and (2) a carrier material in an amount from about 50% by weight to about 99.9% by weight of the composition.

2. The composition of claim 1 wherein said at least one hydrogenated indene-styrene-vinyltoluene polymer has a softening point of between about 70° C. and about 140° C.

3. The composition of claim 2 wherein said hydrogenated indene-styrene-vinyltoluene polymer comprises indene-α-methylstyrene-vinyltoluene polymer.

4. The composition of claim 3 wherein said hydrogenated indene-styrene-vinyltoluene polymer has a softening point of about 125° C.

5. The composition of claim 1 wherein said composition is solid and said carrier material comprises a gelling agent.

6. The composition of claim 5 wherein said gelling agent is dibenzyl monosorbitol acetal.

7. The composition according to claim 1 wherein said carrier material comprises a solvent in which the polymer is miscible.

8. The composition of claim 7 wherein said solvent is selected from the group consisting of octyl methoxycinnamate, phenoxy ethanol, phenyl trimethicone, benzyl alcohol, dibenzyl maleate, methyl benzoate, and mixtures thereof.

9. The composition according to claim 1 wherein said carrier material comprises a solute, said solute being selected from the group consisting of truxillic acid, ferulic acid, ethyl ferulate, and mixtures thereof.

10. The composition of claim 1 wherein said carrier material comprises at least one cosmetically acceptable ester.

11. The composition of claim 10 wherein said cosmetically acceptable ester is selected from the group consisting of mono-esters, di-esters, and tri-esters having an alcohol chain length of 1 to 22 and an acid chain length of 1 to 22.

12. The composition of claim 10 wherein said cosmetically acceptable ester is selected from the group consisting of oils, waxes, glyceryl esters aliphatic esters and fats.

13. The composition according to claim 1 wherein said carrier material comprises a lipophilic oil.

14. The composition according to claim 13 wherein the lipophilic oil is selected from the group consisting of castor oil, mineral oil, squalene, fatty acids, fatty alcohols, a $C_{12-15}$ alkyl benzoate, a propylene glycol dipelargonate, a glycerol trioctanoate and mixtures thereof.

15. The composition according to claim 1 wherein the carrier material comprises a lipophilic wax selected from the group consisting of animal waxes, insect waxes, plant waxes, mineral waxes, petroleum waxes, synthetic waxes and mixtures thereof.

16. The composition according to claim 1 wherein said carrier material is a fluid at room temperature.

17. The composition according to claim 1 wherein the carrier material comprises an ingredient selected from the group consisting of a stabilizer, an antimicrobial agent, an antioxidant, and mixtures thereof.

18. The composition of claim 1 further comprising a cosmetic material in an amount from about 0.5% by weight to about 20% by weight of the composition, wherein said cosmetic material is selected from the group consisting of colorants, fragrances, sunscreens, dermatologic agents, and mixtures thereof.

19. The composition according to claim 18 wherein the cosmetic material is a colorant selected from the group consisting of organic dyes, inorganic dyes, and mixtures thereof.

20. The composition according to claim 18 wherein the cosmetic material is a colorant selected from a group consisting of lipophilic dyes, lakes, pigments and mixtures thereof.

21. The composition according to claim 18 wherein the cosmetic material is a dermatologic agent selected from the group consisting of vitamins, antiinflammatory agents, hydroxy acids, and mixtures thereof.

22. The composition according to claim 18 wherein the cosmetic material comprises a sunscreen selected from the group consisting of dioxybenzone, 2-ethylhexyl 2-cyano-3, 3-diphenylacrylate, 2-ethylhexyl p-methoxycinnamate, 2-ethylhexyl salicylate, homosalate, menthyl anthranilate, oxybenzone, octyl dimethyl PABA, red petrolatum, titanium dioxide, ferulic acid esters and mixtures thereof.

23. The composition according to claim 22 wherein the sunscreen comprises ethyl ferulate.

24. The composition according to claim 22 wherein the sunscreen is titanium dioxide.

25. A method for applying a cosmetic composition to the skin comprising the step of applying to the skin the composition of claim 1.

26. A method for preparing an opalescent composition for topical application to the skin, the composition comprising a hydrogenated indene-styrene-vinyltoluene polymer and a carrier material, the method comprising:

mixing said polymer with at least the carrier material at a temperature and for a period of time sufficient to dissolve said polymer in said carrier material to form a solution, wherein the amounts of said polymer and carrier material being adjusted such that the resulting mixture contains said polymer in an amount from about 0.1% by weight to about 50% by weight of the composition and said carrier material in an amount from about 50% by weight to about 99.9% by weight of the composition.

27. The method according to claim 26, wherein said temperature is greater than room temperature and said method further comprises cooling said composition to room temperature.

28. The method according to claim 26 wherein said mixing step is conducted at a temperature between about 75° C. and about 200° C.

29. The method according to claim 28 wherein said mixing step is conducted at a temperature between about 100° C. and about 150° C.

30. The method of according to claim 26 further comprising mixing a cosmetic material selected from the group consisting of colorants, fragrances, sunscreens, dermatologic agents and mixtures thereof with the solution to form the composition, wherein said cosmetic material is in an amount from about 0.01% by weight to about 20.0% by weight of the composition.

31. The method according to claim 30 further comprising heating at least said carrier material to its melting temperature, and wherein said step of mixing said cosmetic material is conducted prior to, during or after said polymer is mixed with said carrier material.

32. A composition prepared according to the method of claim 26.

33. A composition prepared according to the method of claim 30.

* * * * *